US00PP15232P2

(12) United States Plant Patent
Olesen et al.

(10) Patent No.: US PP15,232 P2
(45) Date of Patent: Oct. 12, 2004

(54) ROSE PLANT NAMED 'POULCS011'

(50) Latin Name: *Rosa hybrida*
Varietal Denomination: POULcs011

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 1 day.

(21) Appl. No.: 10/738,157

(22) Filed: Dec. 16, 2003

(51) Int. Cl.[7] ..... A01H 5/00
(52) U.S. Cl. ..... Plt./143
(58) Field of Search ..... Plt./143

*Primary Examiner*—Anne Marie Grunberg
*Assistant Examiner*—Annette H Para

(57) ABSTRACT

A new garden rose plant of the floribunda class which has abundant pink flowers and attractive foliage. This new and distinct variety has shown to be uniform and stable in the resulting generations from asexual propagation.

2 Drawing Sheets

Botanical classification: *Rosa hybrida.*
Variety denomination: 'POULcs011'.

SUMMARY OF THE INVENTION

The present invention constitutes a new and distinct variety of garden rose plant of the floribunda class which originated from a controlled crossing between a female seed parent, an unnamed seedling, and a male pollen parent plant named 'POULskov', described and illustrated in U.S. Plant Pat. No. 9,062 issued on Feb. 28, 1995. The two parents were crossed during the summer of 1992 and the resulting seeds were planted in a controlled environment in Fredensborg, Denmark. The new variety is named 'POULcs011'.

The new variety may be distinguished from its seed parent, by the following combination of characteristics:

1. The seed parent has fewer than 20 petals. 'POULcs011' has a petal count of 20 to 40.
2. The see parent ha a Red-Purple bud color. The same of 'POULcs011' is Red Group 46A.

The new variety may be distinguished from its pollen parent, 'POULskov' by the following combination of characteristics:

1. The pollen parent has a soft pink coloration while 'POULcs011' is an apricot blend.
2. The pollen parent has a petal count of 48 to 62 whereas 'POULcs011' has 28.

The objective of the hybridization of this rose variety was to create a new and distinct variety for garden use with unique qualities, such as:

1. Uniform and abundant apricot flowers;
2. Continuous flowering;
3. Vigorous, but compact growth when propagated both as a budded rose and on its own roots;
4. Strong rose fragrance;
5. Disease resistance.

This combination of qualities is not present in previously available commercial cultivars of this type, known to the inventors, and distinguish 'POULcs011' from all other varieties of which we are aware.

As part of their rose development program, L. Pernille Olesen and Mogens N. Olesen germinated the seeds from the aforementioned hybridization during winter 1992 and conducted evaluations on the resulting seedlings in a controlled environment in Fredensborg, Denmark.

'POULcs011' was selected in the spring 1993 by the inventors as a single plant from the progeny of the aforementioned hybridization.

Asexual reproduction of 'POULcs011' by traditional budding and rooted cuttings was first done by L. Pernille and Mogens N. Olesen in their nursery in Fredensborg, Denmark in July, 1993. This initial and other subsequent asexual propagations conducted in controlled environments have demonstrated that the characteristics of 'POULcs011' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULcs011'.

Specifically illustrated in SHEET 1:

FIG. 1.1; Open flower, stem showing cluster of open flowers, branching, and the attachment of leaves, buds, and peduncles;

FIG. 1.2; Flower bud closed, flower bud as sepals unfold, and partially open;

FIG. 1.3; Flower petals, detached;

FIG. 1.4; Sepals, receptacle, and peduncle;

Specifically illustrated in SHEET 2:

FIG. 2.1; Mature leaf and juvenile leaf.

FIG. 2.2; Bare stem exhibiting thorns.

DETAILED DESCRIPTION OF THE VARIETY

The following is a description of 'POULcs011', as observed in its growth in a field nursery in Jackson County, Oreg. Observed plants are 3 years of age, grown on *Rosa multiflora* understock. Color references are made using The Royal Horticultural Society (London, England) Colour Chart, 1995, except where common terms of color are used.

For a comparison, several physical characteristics of the rose variety 'POULkalm', a rose variety from the same inventors described and illustrated in U.S. Plant patent application Ser. No. 10/339,733 date Feb. 10, 2003 are compared to 'POULcs011' in Chart 1.

CHART 1

| | 'POULcs011' | 'POULkalm' |
|---|---|---|
| Petal size | 38 mm (1) × 35 mm (w). | 40 mm (1) × 40 mm (w). |
| General tonality | Orange Group 27A. | Blend of Red Group 49B to Orange-Red Group 28D. |
| Bloom diameter | 60 to 70 mm. | 80 to 90 mm. |

Parents:

*Seed parent.*—Unnamed seedling.

*Pollen parent.*—'POULskov'.

FLOWER AND FLOWER BUD

Blooming habit: Continuous.

Flower bud:

*Size.*—Upon opening, 20 mm in length from base of receptacle to end of bud.

*Bud form.*—Short, pointed, and broad-based.

*Bud color.*—As sepals unfold, petals are Red Group 46A. Red Group 36A with intonations of Red Group 46A and Red Group 50B at ¼ opening. Sepals:Upper Surface: Color: Yellow-Green Group 147D. Surface: Moderately pubescent. Lower Surface: Color: Yellow-Green Group 144A with anthocyanic pigments the color of Greyed-Orange Group 176A. Stipitate Glands: Abundant. Shape: Sepal apex is cirrhose. Base is flat at union with receptacle. Margins are entire. No foliaceous appendages on the sepal margins. Size: 25 mm (l)×6 mm (w).

*Receptacle.*—Surface Texture: Smooth and glaucous. Shape: Urn-shaped. Size: 9 mm (h)×6 mm (w). Color: Yellow-Green Group 144A to Green Group 143A.

*Peduncle.*—Surface: Abundant stipitate glands. Length: 40 to 45 mm. Color: Yellow-Green Group 144B. Strength: Strong. Borne: Multiples of 5 buds per flowering stem.

*Flower bloom.*—Fragrance: Strong rose scent. Duration: The blooms have a duration on the plant of approximately 10 to 14 days. Petals fall cleanly away from plant. Size: Average flower diameter is 60 to 70 mm when open. Form: General: Deep cup. Shape of flower when viewed from the side: Upon opening, upper part: Flat. Upon opening, lower part: Concave. Open flower, upper part: Flattened convex. Open flower, lower part: Concave.

*Petalage.*—35 petals under normal conditions with 9 petaloids.

*Color.*—Upon opening, petals: Outermost petals: Outer side: Red Group 36A. Intonations: Red Group 53A to 53B. Inner Side: Red Group 49B. Innermost petals: Outer side: Red Group 36A. Inner Side: Orange Group 27A. Intonations: Red Group 38A.

*Upon opening, basal petal spots.*—Outermost petals: Outer side: Yellow Group 5C. Inner Side: Yellow Group 5C. Innermost petals: Outer side: Yellow Group 5C. Inner Side: Yellow Group 5C.

*After opening, petals.*—Outermost petals: Outer side: Red Group 49D. Inner Side: Red Group 49A. Innermost petals: Outer Side: Orange Group 27D. Inner Side: Orange Group 27A.

*After opening, basal petal spots.*—Outermost petals: Outer side: Yellow Group 9D. Inner side: Yellow Group 9D. Innermost petals: Outer Side: Yellow Group 9D. Inner Side: Yellow Group 9D.

General tonality: On open flower, Orange Group 27A with intonations of Red Group 50D. No change in the general tonality at the end of the 7th day. Afterwards, general tonality is Red Group 49D to White Group 155B with intonations of Red Group 51A to 51B.

Petals:

*Petal reflex.*—Strongly.

*Margin.*—Entire and uniform. Weak undulations of margin.

*Shape.*—Apex: Round. Base: Mildly acute.

*Size.*—38 mm (l)×35 mm (w).

*Texture.*—Smooth.

*Thickness.*—Average.

*Arrangement.*—Not Formal.

Petaloids:

*Quantity.*—8 to 12.

*Color.*—Yellow Group 9D.

Reproductive organs:

*Pistils.*—Length: 8 mm long. Quantity: 45 actual count.

*Pollen.*—None observed.

*Anthers.*—Size: 2 mm long. Color: Yellow-Orange Group 15A. Quantity: 74 actual count.

*Filaments.*—Color: Yellow Group 5B. Length: 6 mm.

*Stigmas.*—Superior in location to length of filaments and height of the anthers. Color: Greyed-Yellow Group 162A.

*Styles.*—Color: Red Group 38A.

*Hips.*—None Observed in the field nursery in Jackson County, Oreg.

Plant growth: Moderate, upright to bushy. When grown as a budded field grown plant on *Rosa multiflora* understock, the average height of the plant is 60 cm to 100 cm. Average spread is 60 cm.

Stems:

*Color.*—Young wood: Yellow-Green Group 146C. Older wood: Yellow-Green Group 144A.

*Surface texture.*—Young wood: Smooth. Older wood: Smooth.

*Thorns.*—Incidence: 6 thorns per 10 cm of stem. Size: 7 mm in length. Color: Greyed-Orange Group 175A. Shape: Deeply concave.

Plant foliage: Normal number of leaflets on normal leaves in middle of the stem: 7 leaflets.

*Size.*—130 mm (l)×85 mm (w).

*Color.*—Mature Foliage: Upper Leaf Surface: Yellow-Green Group 146A. Lower Leaf Surface: Yellow-Green Group 146B. Juvenile foliage: Upper Leaf Surface: Yellow-Green Group 144A. Lower Leaf Surface: Yellow-Green Group 144B. Anthocyanin: Location: Rachis and leaf margins of juvenile foliage. Color: Greyed-Purple Group 183A.

Plant leaves and leaflets:

*Stipules.*—Size: 20 mm in length. Color: Yellow-Green Group 146A.

*Petiole.*—Length: 35 mm. Color: Yellow-Green Group 144B. Underneath: Thorns observed. Margins: Stipitate glands sparsely present.

*Rachis.*—Length: 50 mm. Color: Yellow-Green Group 144B. Underneath: Thorns observed. Margins: Stipitate glands sparsely present.

*Leaflet.*—Size: 45 mm (l)×38 mm (w). Edge: Serrated. Shape: Ovate to round. Apex is cuspidate. Bases is rounded. Texture: Smooth. Arrangement: Odd pinnate. Venation: Reticulate. Glossiness: Glossy. Thickness: Very thick.

Disease resistance: Above average resistance to mildew, rust, black spot, and Botrytis under normal growing conditions in Jackson County, Oreg.

Cold hardiness: The variety 'POULcs011' has been found to be cold tolerant to USDA Cold Hardiness Zone 6.

It is claimed:

1. A new and distinct variety of rose plant of the floribunda rose class, substantially as herein illustrated and described as a distinct and novel rose variety due to its abundant pink flowers, exceptional fragrance, disease resistance, and extended period of bloom.

* * * * *

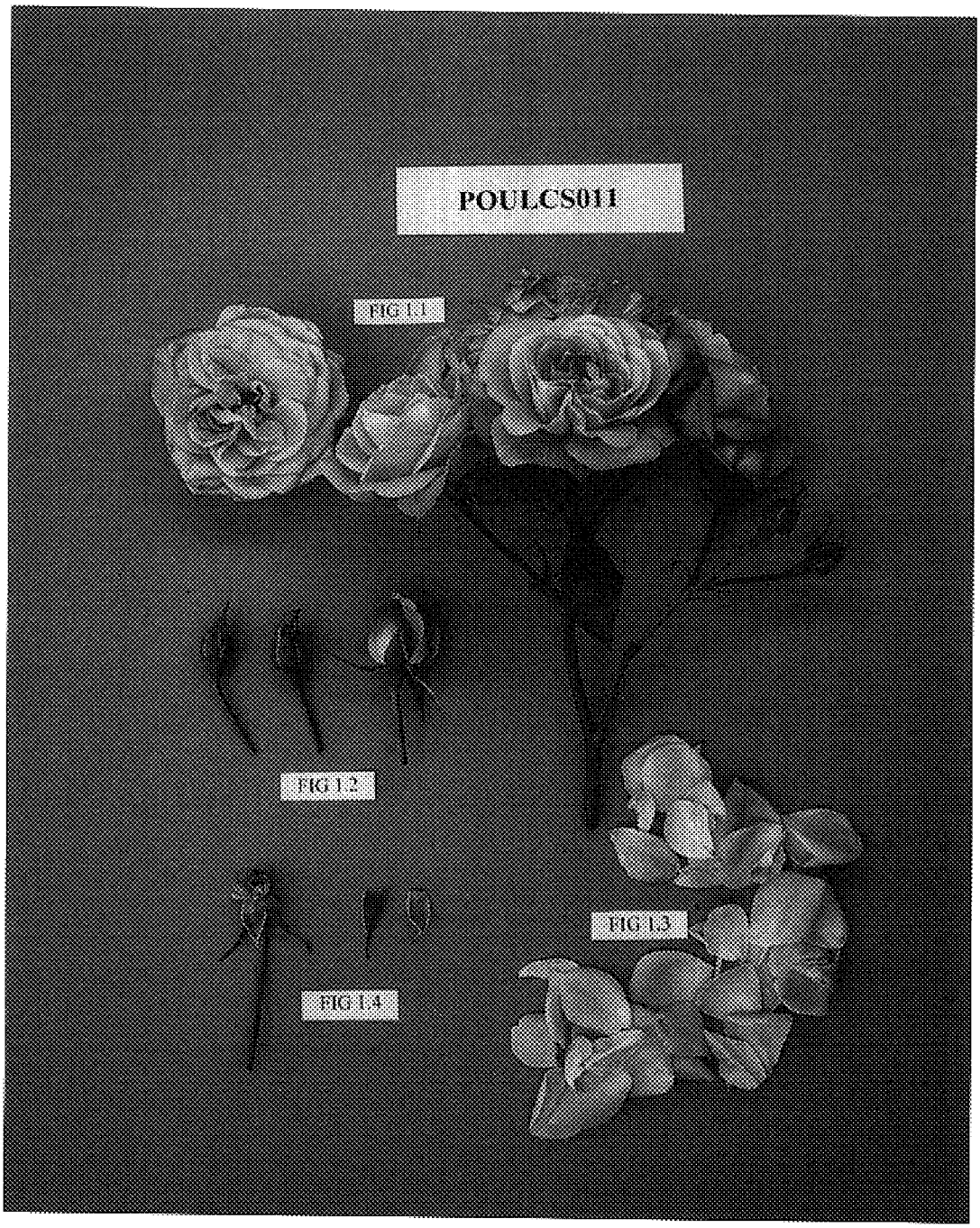
POULCS011
FIG 1.1
FIG 1.2
FIG 1.3
FIG 1.4

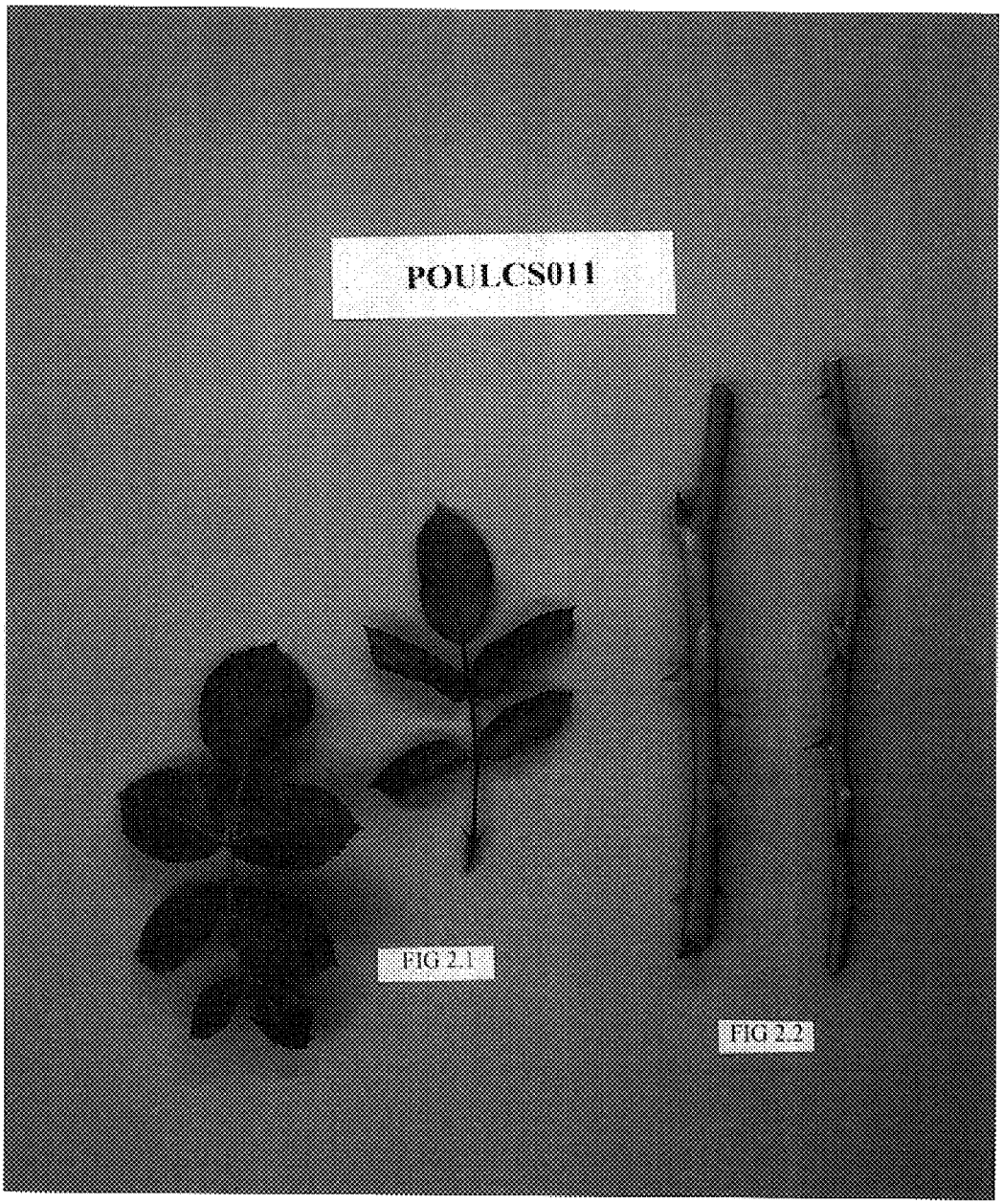
POULCS011
FIG 2.1
FIG 2.2